(12) United States Patent
Drain

(10) Patent No.: US 10,952,775 B1
(45) Date of Patent: Mar. 23, 2021

(54) SURGICAL INSTRUMENT WITH ORIENTATION SENSOR HAVING A USER IDENTIFIED HEADING

(71) Applicant: Prichard Medical, LLC, Rocky River, OH (US)

(72) Inventor: Joseph Prichard Drain, Rocky River, OH (US)

(73) Assignee: Prichard Medical, LLC, Rocky River, OH (US)

( * ) Notice: Subject to any disclaimer, the term of this patent is extended or adjusted under 35 U.S.C. 154(b) by 0 days.

(21) Appl. No.: 17/121,006

(22) Filed: Dec. 14, 2020

(51) Int. Cl.
*A61B 17/66* (2006.01)
*G16H 40/63* (2018.01)
*A61B 17/00* (2006.01)

(52) U.S. Cl.
CPC .............. *A61B 17/66* (2013.01); *G16H 40/63* (2018.01); *A61B 2017/00199* (2013.01); *A61B 2017/00455* (2013.01); *A61B 2560/0487* (2013.01)

(58) Field of Classification Search
CPC .......... A61B 17/66; A61B 2017/00199; A61B 2017/00455; A61B 2560/0487; G16H 40/63
See application file for complete search history.

(56) References Cited

U.S. PATENT DOCUMENTS

| 5,953,683 | A | 9/1999 | Hansen et al. |
|---|---|---|---|
| 7,559,931 | B2 | 7/2009 | Stone |
| 8,057,482 | B2 | 11/2011 | Stone et al. |
| 8,118,815 | B2 | 2/2012 | Van der Walt |
| 8,241,296 | B2 | 8/2012 | Wasielewski |
| 8,740,810 | B2 | 6/2014 | Sanbuichi |
| 8,814,877 | B2 | 8/2014 | Wasielewski |
| 9,532,730 | B2 | 1/2017 | Wasielewski |

(Continued)

FOREIGN PATENT DOCUMENTS

| EP | 1635705 B1 | 1/2012 |
|---|---|---|
| WO | WO 2009/055034 A1 | 4/2009 |
| WO | WO 2013/169674 A1 | 11/2013 |

OTHER PUBLICATIONS

Bosch Sensortec; BNO055 Intelligent 9-axis absolute orientation sensor; Data Sheet; Document Revision 1.4; Date Jun. 2016; Doc. No. BST-BNO055-DS00-14; 106 pages.

(Continued)

*Primary Examiner* — George Manuel
(74) *Attorney, Agent, or Firm* — BakerHostetler; Cory N. Nesemann

(57) ABSTRACT

An orientation sensor that includes a user input device that is configured to set a heading of the orientation sensor based on an orientation of the orientation sensor. The orientation sensor may include a memory that is configured to store the heading. The orientation sensor may include a display that is configured to display the at least one orientation value. The orientation sensor may include a processor that is configured to generate orientation information based on the heading. The user input device may include a button, and in response to pressing the button the heading may be set based on the current orientation of the orientation sensor. For example, the at least one orientation value may be associated with orientation data detected by an orientation sensing component, and the at least one orientation value may be displayed based on the heading.

26 Claims, 12 Drawing Sheets

(56) References Cited

U.S. PATENT DOCUMENTS

| | | |
|---|---|---|
| 9,795,451 B2 | 10/2017 | Gorek et al. |
| 2009/0318836 A1 | 12/2009 | Stone et al. |
| 2010/0076505 A1 | 3/2010 | Borja |
| 2010/0125172 A1 | 5/2010 | Jayaray |
| 2010/0137869 A1 | 6/2010 | Borja |
| 2011/0208093 A1 | 8/2011 | Gross et al. |
| 2011/0313281 A1 | 12/2011 | Grinberg et al. |
| 2012/0319859 A1 | 12/2012 | Taub et al. |
| 2014/0030669 A1 | 1/2014 | Hey et al. |
| 2014/0052149 A1 | 2/2014 | Van der Walt et al. |
| 2015/0119637 A1 | 4/2015 | Alvarez et al. |
| 2015/0127009 A1 | 5/2015 | Berend |
| 2015/0223890 A1* | 8/2015 | Miller ................. G06F 21/6245 705/2 |
| 2015/0238204 A1 | 8/2015 | Stone |
| 2015/0272696 A1 | 10/2015 | Fry et al. |
| 2015/0305786 A1 | 10/2015 | Wehrle et al. |
| 2015/0366714 A1 | 12/2015 | Kandavel et al. |
| 2016/0242934 A1 | 8/2016 | Van der Walt et al. |
| 2016/0310077 A1 | 10/2016 | Hunter et al. |
| 2016/0354162 A1 | 12/2016 | Yen et al. |
| 2017/0172458 A1 | 6/2017 | Kato et al. |
| 2018/0058536 A1 | 3/2018 | Pathak et al. |
| 2018/0110569 A1 | 4/2018 | Drain |
| 2018/0193171 A1 | 7/2018 | Van der Walt et al. |
| 2020/0237446 A1 | 7/2020 | Drain |

OTHER PUBLICATIONS

International Patent Application No. PCT/US2020/029882; Int' Written Opinion and Search Report; dated Aug. 3, 2020; 12 pages.

\* cited by examiner

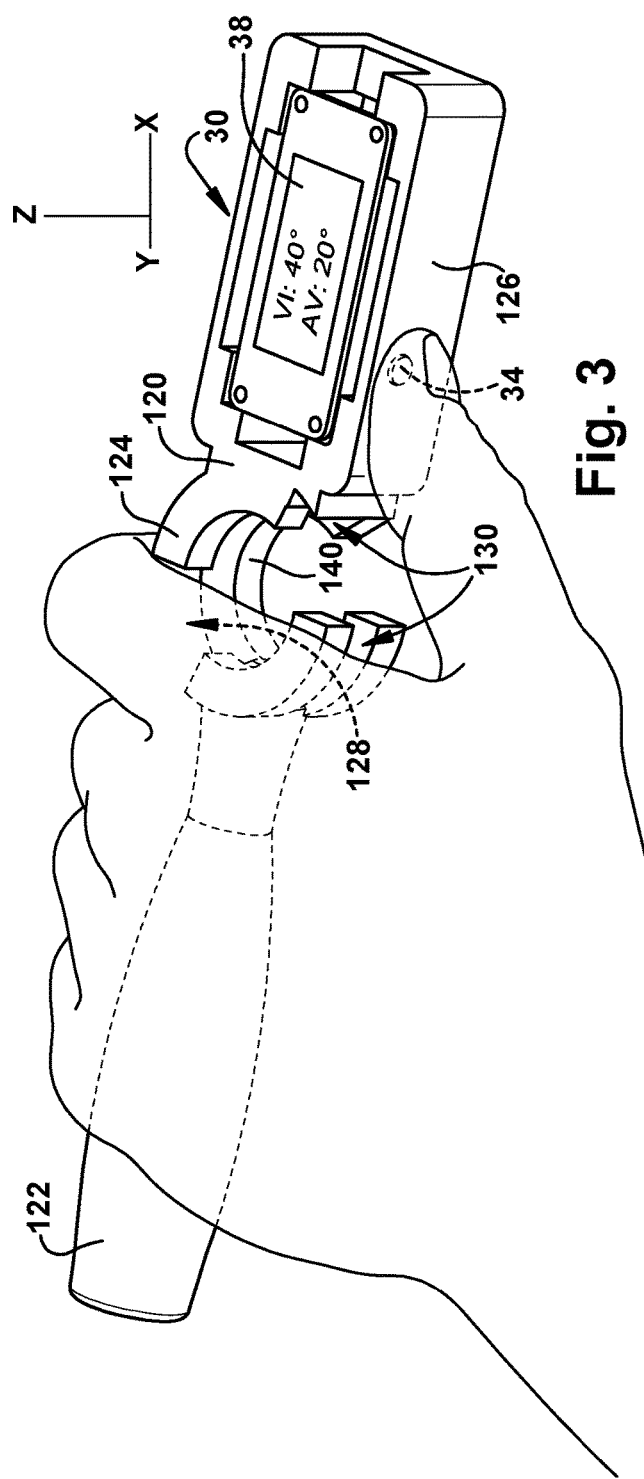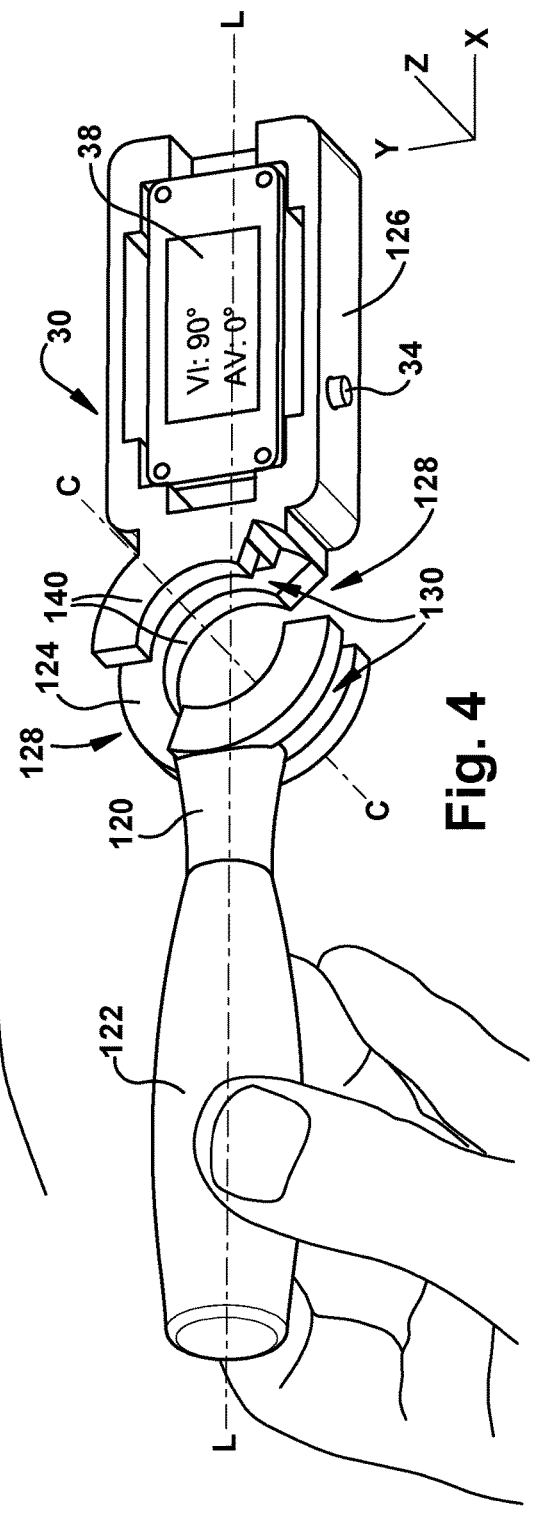

SURGICAL INSTRUMENT WITH ORIENTATION SENSOR HAVING A USER IDENTIFIED HEADING

FIELD OF INVENTION

The disclosure relates generally to instruments, such as medical (e.g., surgical) instruments. For example, this disclosure relates to surgical and other medical instruments including absolute orientation sensors. The instruments of the present disclosure may be used in any suitable procedure or treatment which would benefit from knowing the orientation of such instrument in three-dimensional space. While reference is made herein to surgical instruments in particular, it should be understood that this disclosure is directed to medical, dental, or other instruments used in the treatment of humans or animals requiring orientation knowledge.

BACKGROUND

Some medical procedures rely upon a medical practitioner aligning tools by eye or with a cumbersome alignment guide. For example, when performing a hip replacement surgery a surgeon may use an impactor shaft to install an acetabular cup. The surgeon may use an anteversion guide or an alignment extension to orient the impactor shaft at a 20-degree (20°) anteversion angle relative to a longitudinal body axis of a patient. Also, the surgeon may use an alignment extension to orient an impactor shaft at a 45-degree (45°) inclination/abduction angle relative to the longitudinal body axis of the patient (and relative to a horizontal plane when the patient is lying on their side).

When alignment of the impactor shaft is not proper, misalignment of the acetabular cup occurs, which can cause complications after surgery to arise. Additional surgery may be required to correct the misalignment resulting from the original installation of the acetabular cup.

SUMMARY

The present application provides an orientation sensor that includes a user input device that is configured to set a heading of the orientation sensor based on an orientation of the orientation sensor. The orientation sensor may include a memory that is configured to store the heading. The orientation sensor may include a display that is configured to display the at least one orientation value. The orientation sensor may include a processor that is configured to generate orientation information based on the heading. The user input device may include a button, and in response to pressing the button the heading may be set based on the current orientation of the orientation sensor. For example, the at least one orientation value may be associated with orientation data detected by an orientation sensing component, and the at least one orientation value may be displayed based on the heading.

The display may provide the surgeon with real-time feedback of angles that are pertinent to a given surgery. For example, the surgeon may align an axis (e.g., the longitudinal axis) of the orientation sensor with an axis (e.g., a longitudinal body axis) of the patient and provide a predetermined input to the user input device (e.g., press a button of the user input device) to set a heading for the orientation sensor. When the heading is set, the display may display in real-time an angle of an instrument axis (e.g., a central axis of a guide) of the orientation sensor relative to the longitudinal body axis of the patient. For example, the anteversion angle and vertical inclination angle of the central axis of the guide may be displayed in real-time relative to the longitudinal body axis of a patient lying on their side. In an embodiment, the heading may be set to a different axis of the patient and anteversion angle and the vertical inclination angle of the central axis may be displayed in real-time relative to the different axis.

The orientation sensor may be configured to mount to an instrument body. For example, the orientation sensor may include a guide that is configured to receive a shaft of an instrument body as disclosed in U.S. patent application Ser. No. 16/395,986 filed on Apr. 26, 2019 and U.S. patent application Ser. No. 15/619,747 filed on Jun. 12, 2017, both of which both of which are entitled Surgical Instrument With LED Lighting and Absolute Orientation and are hereby incorporated by reference in their entirety. In an embodiment, the surgical instrument includes a housing or other outer structure to which the orientation sensor is configured to be attached or affixed.

The following presents a simplified overview of the example embodiments in order to provide a basic understanding of some aspects of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented later.

In accordance with embodiments herein, the present disclosure provides medical instruments and devices having orientation sensors (e.g., absolute orientation sensors) with a button that sets the heading of the orientation sensor based on the orientation of the orientation sensor in response to the button being pressed. The instruments of the present disclosure may be used in any suitable procedure or treatment which would benefit from knowing the orientation of the surgical instrument in relation to a heading set by the user (e.g., the surgeon).

While reference is made herein to surgical instruments in particular, it should be understood that this disclosure is applicable to medical, dental, or other instruments used in the treatment of humans or animals requiring orientation.

An absolute orientation sensor may not require calibration against a known point or plane in order to provide orientation related information. For example, an embodiment of an absolute orientation sensor comprises an accelerometer, a gyroscope, and a magnetometer, and may be able to generate an absolute orientation by using the Earth itself as a reference point or plane, by sensing the Earth's magnetic field, and by extension, the Earth's magnetic core, rather than an arbitrarily determined point or plane. In some embodiments, the orientation sensor does not include a magnetometer. For example, the heading of the orientation sensor may be manually set by the user, as opposed to being set to an arbitrary angle upon activation of the orientation sensor or being set to magnetic north.

According to one aspect of the invention, an orientation sensor comprises: a processor; an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; a display operably coupled to the processor, wherein the display is configured to display at least one orientation value, that is associated with the plurality of orientation data, in real-time; a user input device operably coupled to the processor, wherein the processor is configured to, in response to the user input device receiving a predetermined user input, set a heading based on the orientation of the orientation sensor when the predetermined user input is received by the user input device; wherein the heading is associated with the orientation data such that when the orientation sensor would be held in a predetermined reference orientation relative to the heading, the display displays a predetermined orientation value, and whereby movement of the orientation sensing component in the at least one direction from the predetermined reference orientation would be represented on the display as the at least one orientation value being different from the predetermined orientation value.

According to another aspect of the invention, an orientation sensor comprises: a processor; a memory operably coupled to the processor; an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component; a user input device operably coupled to the processor, wherein, in response to the user input device receiving a predetermined user input, the processor is configured to store, in the memory, a heading based on the orientation of the orientation sensor when the predetermined user input is received by the user input device; wherein the processor is configured to generate orientation information based on the heading, that is stored in the memory, and the current orientation of the orientation sensor; and wherein the heading is associated with the orientation data such that when the orientation sensor would be held in a predetermined reference orientation relative to the heading, processor generates predetermined orientation information, and whereby movement of the orientation sensing component in the at least one direction from the predetermined reference orientation would be represented by the processor generating a first orientation information that is different from the predetermined orientation information.

Features of any of the above aspects may be combined with one another. For example, any above aspect may include the display, processor, and/or memory of another aspect.

In addition or alternatively, any above aspect may be a part of a surgical instrument. For example, any orientation sensor may be removable from an instrument body of a surgical instrument.

The surgical instrument may comprise a display operatively coupled to the device processor, wherein the display may be operable to display at least a portion of the plurality of generated orientation status data thereon. The plurality of orientation data may comprise at least one from the group consisting of a location data, pitch data, roll data, and yaw data. The location data may comprise x, y, and z coordinate values. The plurality of orientation data may further comprise at least one selected from the group consisting of angular velocity data, acceleration data, magnetic field strength data, linear acceleration data, and gravity data.

The surgical instrument may be one or more: drills, drivers, saws, wire insertion devices, impactors, device inserters, burr, awls, scalpels, suction, retraction devices, mallets, biopsy needles, unpowered drills, unpowered drivers, unpowered saws, unpowered wire inserters, and/or unpowered burrs.

Still other advantages, aspects and features of the subject disclosure will become readily apparent to those skilled in the art from the following description wherein there is shown and described embodiments of the present disclosure, simply by way of illustration of modes suited to carry out the subject disclosure. As it will be realized, the present disclosure is capable of other different embodiments and its several details are capable of modifications in various obvious aspects all without departing from the scope herein. Accordingly, the drawings and descriptions will be regarded as illustrative in nature and not as restrictive.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

FIG. 3 is an oblique view of the orientation sensor of FIG. 1 while a heading is being set.

FIG. 4 is an oblique view of the orientation sensor of FIG. 1 after a heading has been set and the orientation sensor is oriented to a predetermined reference orientation relative to the heading.

DETAILED DESCRIPTION

Figure 1:
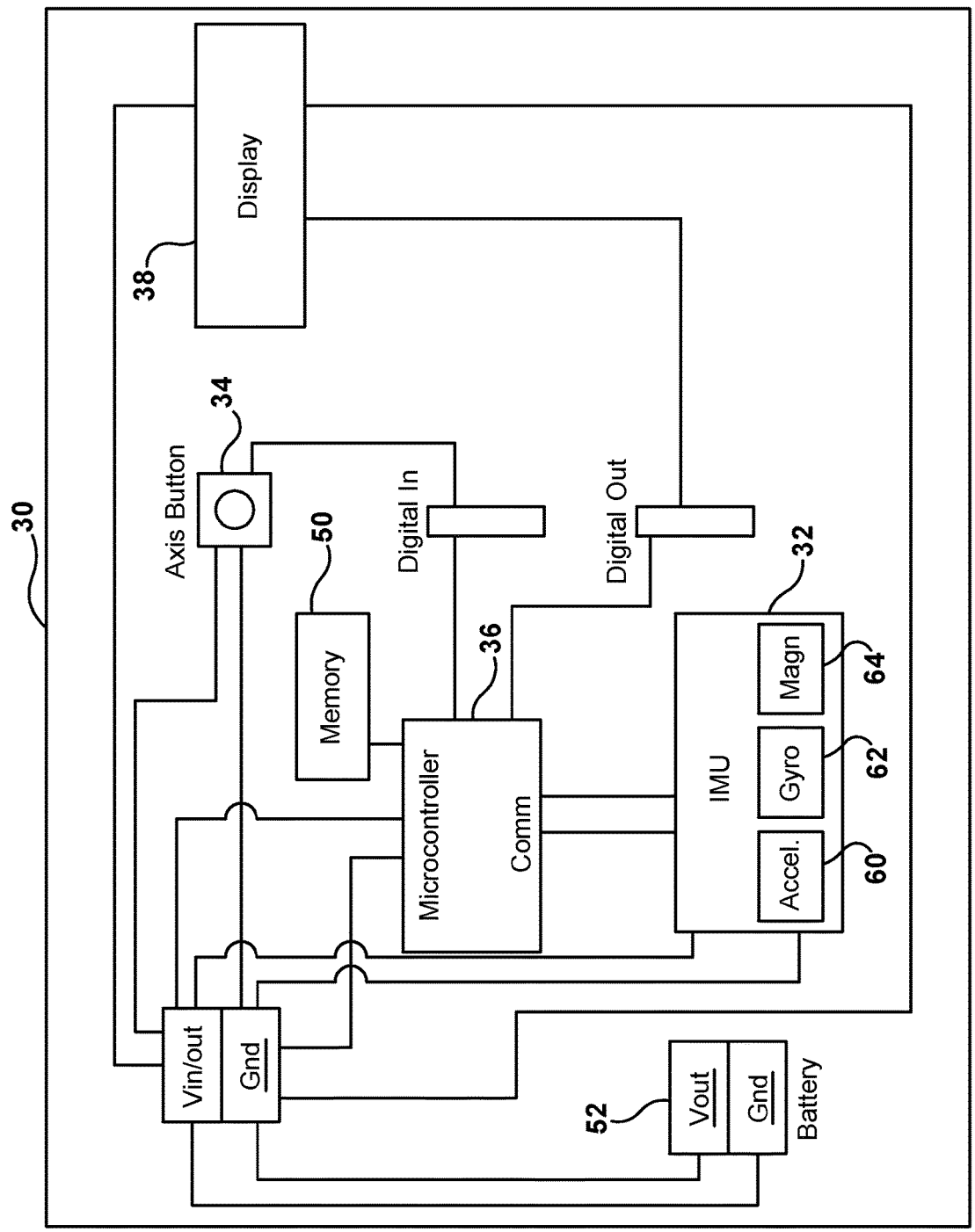
FIG. 1 is a block diagram of an orientation sensor that includes a user input device.

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware embodiments. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including any non-transient computer-readable storage medium (e.g., hard disks, CD-ROMs, optical storage devices, and/or magnetic storage devices).

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, may be implemented by special purpose hardware-based computer systems that perform the specified functions or steps, or combinations of special purpose hardware and computer instructions.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

FIG. 1 is a block diagram of an orientation sensor 30. The orientation sensor 30 (e.g., an absolute orientation sensor) may include an orientation sensing component 32 (e.g., a 6-axis inertial measurement unit (IMU), or an absolute orientation sensing component, such as a 9-axis IMU), a user input device 34, a processor 36, and/or a display 38. The orientation sensor 30 may include a memory 50, and/or a power source 52.

The user input device 34 may be operably coupled to the processor 36. For example, the user input device 34 may be configured to communicate a predetermined user input and/or other user inputs to the processor 36 and/or the memory 50. In an embodiment, the user input device includes a touchscreen display, a biometric interface, and/or a motion sensor. For example, the user input device may include one or more controls that allow the user to interact with and input information and/or commands to the orientation sensor and/or surgical instrument via the processor and/or the memory.

The orientation sensing component 32 may be configured to generate an absolute orientation by using the Earth itself as a reference point or plane, by sensing the Earth's magnetic field, and by extension, the Earth's magnetic core, rather than an arbitrarily determined point or plane. For example, the orientation sensing component 32 may include an accelerometer 60, a gyroscope 62, and a magnetometer 64. For example, when initially turned on the orientation sensing component 32 may generate an absolute orientation based upon an X-axis and a Y-axis that are perpendicular to one another and parallel to a horizontal plane planar with the surface of the Earth, and based upon a Z-axis (i.e., a vertical axis) that is perpendicular to the X-axis and the Y-axis. In an embodiment, when the orientation sensing component is activated (e.g., powered on or reset) the X-axis or the Y-axis is aligned with a predetermined portion of the orientation sensor (e.g., a longitudinal axis of the orientation sensor). In another embodiment, the X-axis or the Y-axis is colinear with a northward direction (e.g., magnetic north).

When the orientation sensor 30 is mounted to a surgical instrument (e.g., the impactor exemplified in FIG. 9) 100, the orientation of the orientation sensor 30 may be extrapolated to determine the orientation of the surgical instrument 100 (e.g., the orientation of a shaft 102 of the surgical instrument 100). At least part of the orientation of the surgical instrument 100 may be displayed with the display 38 such that a user can view the at least part of the orientation. For example, the display may be configured to display angles of inclination of the orientation sensor 30 relative to the Z-axis (e.g., as a vertical inclination angle) and the X-axis (e.g., as an anteversion angle). In an embodiment, orientation information and/or orientation data generated by the orientation sensing component is transmitted to an external electronic device (e.g., a display external to the surgical instrument).

The orientation sensor 30 is mountable to the surgical instrument 100. In an embodiment, the orientation sensor is mountable to substantially any surgical device.

The accelerometer 60 may be configured to measure linear acceleration. The accelerometer 60 may be a multi-axis accelerometer. When the accelerometer 60 is at rest relative to the surface of the Earth may measure a positive acceleration of 9.81 m/s, and when the accelerometer 60 is in free fall towards the center of the Earth the accelerometer 60 may measure an acceleration of 0 m/s.

The gyroscope 62 may include a spinning wheel or disc in which the axis of rotation is free to assume any orientation by itself, or may include a microelectricalmechanical system (MEMS). The gyroscope 62 may be configured to measure or maintain orientation, and/or provide information about angular acceleration, velocity, and/or position.

The magnetometer 64 may be configured to measure magnetism—including either magnetization of magnetic material like a ferromagnet, or the direction, strength, or the relative change of a magnetic field at a particular location. For example, the magnetometer 64 may be a multiaxial geomagnetic sensor.

The power source 52 may provide power to the orientation sensor 30, the device processor 36, and/or the display 38. The power source 52 may be a battery that is mechanically fixed relative to a body of the orientation sensor. In an embodiment, the power source is any other suitable component, such as a power source for the tool.

The processor 36 may be operatively coupled to, and control, the orientation sensor 30 and the display 38. In an embodiment, the orientation sensor includes an input/output device (e.g., transmitter/receiver) that is operably coupled to the processor 36.

The processor 36 may be, or may comprise, any suitable microprocessor or microcontroller. The processor 36 may be coupled (e.g., communicatively, operatively, etc.) to auxiliary devices or modules of the surgical instrument 100 using a bus or other coupling.

The orientation sensing component 32 may capture, in real-time, various orientation variables of the surgical instrument 100, including location, position (e.g., pitch, roll, and yaw) angular acceleration, velocity, linear acceleration. The orientation sensing component 32 may also capture, in real-time, magnetic field strength, gravity, and/or temperature. For example, the location of the surgical instrument 100 may include x, y, and z coordinate values, and other indicators of position and/or orientation in three-dimensional space.

The orientation sensor 30 may be configured to generate orientation information that is particular to the tool being used. For example, when the orientation sensor 30 is mounted on the surgical instrument 100, the orientation information generated by the orientation sensor 30 may include information associated with the location, the pitch, the roll, and/or the yaw of the tip, shaft 102, or active portion of the surgical instrument 100 (e.g., a drill portion of an awl, or another device or tool).

The orientation sensor 30 may be calibrated such that the orientation information generated by the orientation sensor 30 is based on the tip, shaft 102, or active portion of the surgical instrument 100 by the processor 36 calculating differences in orientation of the orientation sensor 30 and tip or active portion of the surgical instrument 100. For example, as discussed in more detail below, orientation information associated with a measured axis may be associated with a heading axis (e.g., a longitudinal axis) of the orientation sensor 30 and/or of the surgical instrument. In an embodiment, orientation information associated with more than one measured axis may be associated with respective axes of the orientation sensor and/or of the surgical instrument.

The orientation sensing component 32 may be configured to self-calibrate itself in relation to a horizontal plane and a vertical axis the Earth's magnetic field and/or the Earth's core as reference points or planes. For example, the orientation sensing component 32 may associate an X-axis and a Y-axis with a horizontal plane—e.g., parallel to a plane tangent to the Earth's surface—and a Z-axis with a vertical axis—e.g., parallel to an axis extending through the Earth's core.

The orientation sensing component 32 may be configured to generate orientation data comprising quaternion(s), Euler angle(s), rotation vector(s), linear acceleration(s), gravity, and/or a heading.

The orientation sensor 30, as discussed above, may be an absolute orientation sensor that may generate orientation values that are relative to the X-axis, the Y-axis, and/or the Z-axis. For example, the processor 36 may be configured to receive the orientation data from the orientation sensing component 32 and output orientation information to be displayed by the display. The orientation information may include data that represents a measured inclination relative to the X-axis, the Y-axis, and/or the Z-axis. For example, as discussed in more detail below, the orientation information may include data that represents a measured inclination relative to a user-identified X-axis, the Y-axis perpendicular to the X-axis, and the Z-axis perpendicular to the X-axis and the Y-axis. The orientation information may include data that represents a measured rotation (e.g., synchronous rotation) relative to the Y-axis, a measured rotation (e.g., synchronous rotation) relative to the Z-axis, and/or a measured rotation (e.g., synchronous rotation) relative to the X-axis.

In an embodiment, the orientation information includes data representing all of the measured orientation data in relation to the X-axis, the Y-axis, and/or the Z-axis. In other embodiments, the orientation information includes data representing any combination of the measured orientation data in relation to the X-axis, the Y-axis, and/or the Z-axis.

Movement of the surgical instrument may result in the display displaying the orientation information in real-time. For example, the rotation about the X-axis, the Y-axis, and/or the Z-axis may be displayed in real-time by the display 38—with or without an adjustment depending on the particular tool or type of procedure. As discussed in more detail below, the rotation about the Y-axis may be displayed as an anteversion angle of the tool and the rotation about the Z-axis may be displayed as an inclination angle of the tool.

The display may be visible by the user (e.g., a surgeon) during use (e.g., during a surgery). For example, the display may be configured to display the orientation data to for a surgeon to view when the angle of the tool is not easily discernable by the surgeon. The display provides for the surgeon to discern the precise orientation of the tool when the tool is at least partially inside the patient, even when a significant portion of the tool is not visible to the surgeon.

The processor 36 may transmit a signal comprising the orientation information to the display 38. The display 38 may digitally display orientation values that represent the orientation information such that the user may read the orientation values on the display 38. In an embodiment, the display is configured to display the orientation values at a location remote from the body of the orientation sensor 30 and the tool. For example, the input/output device may transmit the orientation information to an external display (e.g., a monitor mounted on a wall in the surgical room).

In some embodiments, the display or another display is configured to display a predetermined light signal when a predetermined orientation condition of the tool (e.g., a predetermined rotation about one of the axes) is met. The color or intensity of the light signal may be based on how far the tool is outside and/or inside the predetermined orientation condition.

In some embodiments, in addition to or alternatively to the display an audio device is configured to generate a sound when a predetermined orientation condition of the tool (e.g., a predetermined rotation about one of the axes) is met. The type or intensity of the sound may be based on how far the tool is outside and/or inside the predetermined orientation condition.

Figure 2:
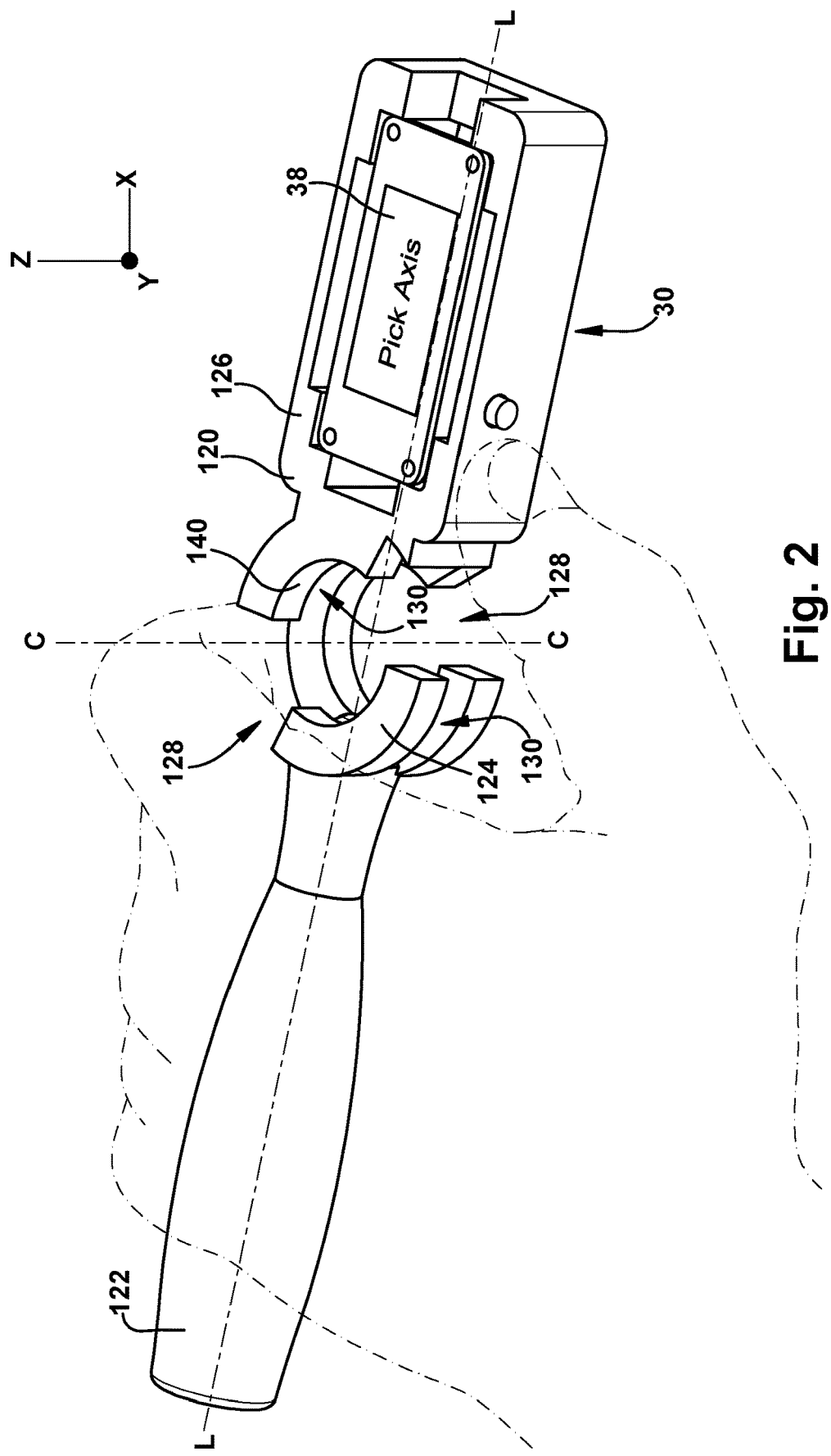
FIG. 2 is an oblique view of the orientation sensor of FIG. 1.
Figure 9:
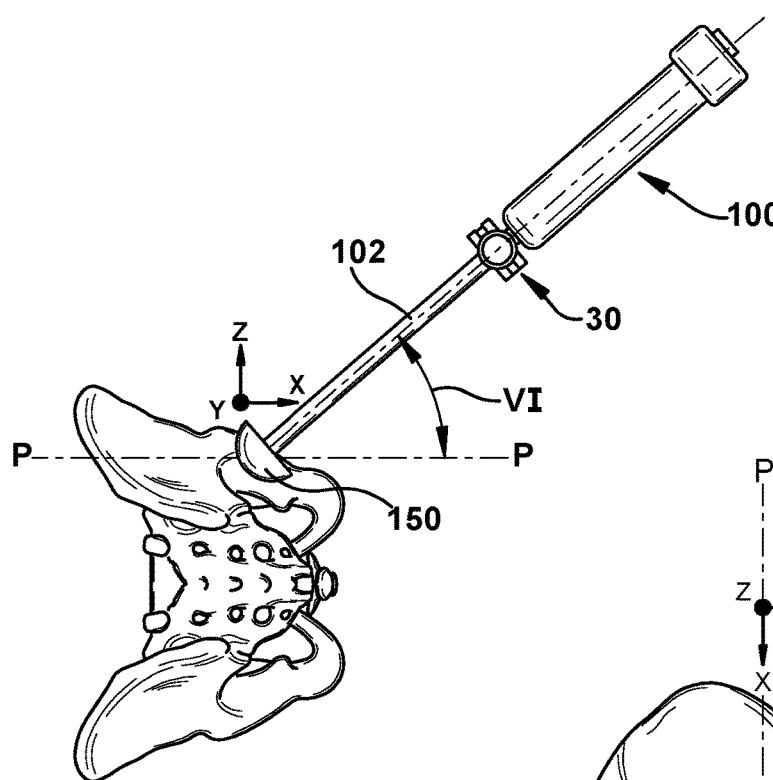
FIG. 9 is a posterior to anterior view of the pelvis in combination with the orientation sensor of FIG. 7 and a surgical instrument.

FIGS. 2-4 illustrate an example of the orientation sensor 30 that is configured to receive a part of the tool (e.g., the shaft 102 of the impactor, as exemplified in FIG. 9). The orientation sensor may include a sensor body 120. The sensor body 120 may define a handle 122, a guide 124, and/or a display arm 126.

The display 38 may be mounted to the display arm 126. For example, the display 38 may be oriented to face in a display direction perpendicular to a longitudinal sensor body axis L. As discussed above, the display 38 portion may display the current orientation of the orientation sensor 30 (e.g., within a hundredth of a second in real-time).

The handle 122 may be configured to be held in the hand of a surgeon. For example, the handle 122 may be elongate along the longitudinal sensor body axis L. In an embodiment, the handle includes at least some of the electronical components of the orientation sensor. For example, the handle may include the processor, the user input device, the orientation sensing component, and/or the power source.

The display arm 126 may be elongate along the longitudinal sensor body axis L. The display arm 126 may be fixed relative to the handle 122 and/or at least part of the guide 124. In some embodiments, the display arm is configured to move relative to the handle. For example, in an embodiment, the display arm is rotatable about one or more axes (e.g., a lateral axis that is transverse to the longitudinal sensor body axis) relative to the handle as discussed in U.S. patent application Ser. No. 16/395,986 filed on Apr. 26, 2019.

The display arm 126 may include at least some of the electronical components of the orientation sensor. For example, the display arm 126 may include the processor 36, the user input device 34, the orientation sensing component 32, the power source 52, and/or the display 38 (shown in FIG. 1). In an embodiment, any of or any combination of the processor, the user input device, the orientation sensing component, the power source, and/or the display is mounted to another component of the orientation sensor.

The guide 124 may be fixed relative to the handle 122. The guide 124 may be configured to mount to the tool 100 (e.g., the shaft 102 of the impactor). For example, the guide 124 may be configured to receive the shaft 102 and/or attach to the tool 100. In some embodiments, the guide or another portion of the orientation sensor is a different shape to mount to a different surgical tool.

When mounted, the guide 124 may substantially circumscribe a portion of the shaft 102. For example, the guide 124 may include lateral opening (e.g., to receive the shaft 102 of the tool 100 in a lateral direction). In an embodiment, the guide entirely circumscribes a portion of the shaft when mounted.

A radially outer portion of the guide 124 may include one or more longitudinally extending notches 128, along a central guide axis C of the guide 124, that connect to a respective circumferentially extending slot 130. The circumferentially extending slot 130 may be open at only one circumferential end such that the other circumferential end is formed by a wall.

As shown in FIGS. 2-4 the inner surfaces 140 of the guide 124 may curved about the central guide axis C. The central guide axis C may be colinear or parallel with the shaft 102 of the tool 100 when the guide 124 is mounted to the tool 100. For example, each inner surface 140 may conform to a generally cylindrical shape (e.g., the shaft 102 of the impactor).

When the tool 100 is in a mounted position in the guide 124, the guide 124 and/or the sensor body 120 may be only rotatable about the shaft 102 of the tool 100. The user may manually restrain relative movement of the guide 124 and the tool 100 by holding the handle 122 of the orientation sensor 30 and the handle 122 of the tool 100 together (e.g., with a single hand). In an embodiment, the guide is configured to be entirely fixed relative to the impactor when the guide is mounted to the impactor such movement of the guide relative to the impactor in every direction is prevented.

The absolute orientation sensing component 32 may be configured to be removable from the instrument body by hand. For example, the entire orientation sensor 30 may be rotated from the mounted position relative to the impactor and removed from the impactor shaft by hand (i.e., without a tool) by sliding and/or laterally moving the shaft through an opening of the guide 124.

In an embodiment, the guide includes a bearing that is configured to slide and/or rotated about a shaft of the tool. For example, the bearing may include an inner cylinder that is configured to rotate relative to and outer cylinder separated from the inner cylinder by ball bearings. In some embodiments, the guide includes a cylindrical bushing that is i) disposed within an outer guide body that is fixed relative to the handle, and ii) configured to slide and/or rotate about a shaft of the tool.

Figure 10:
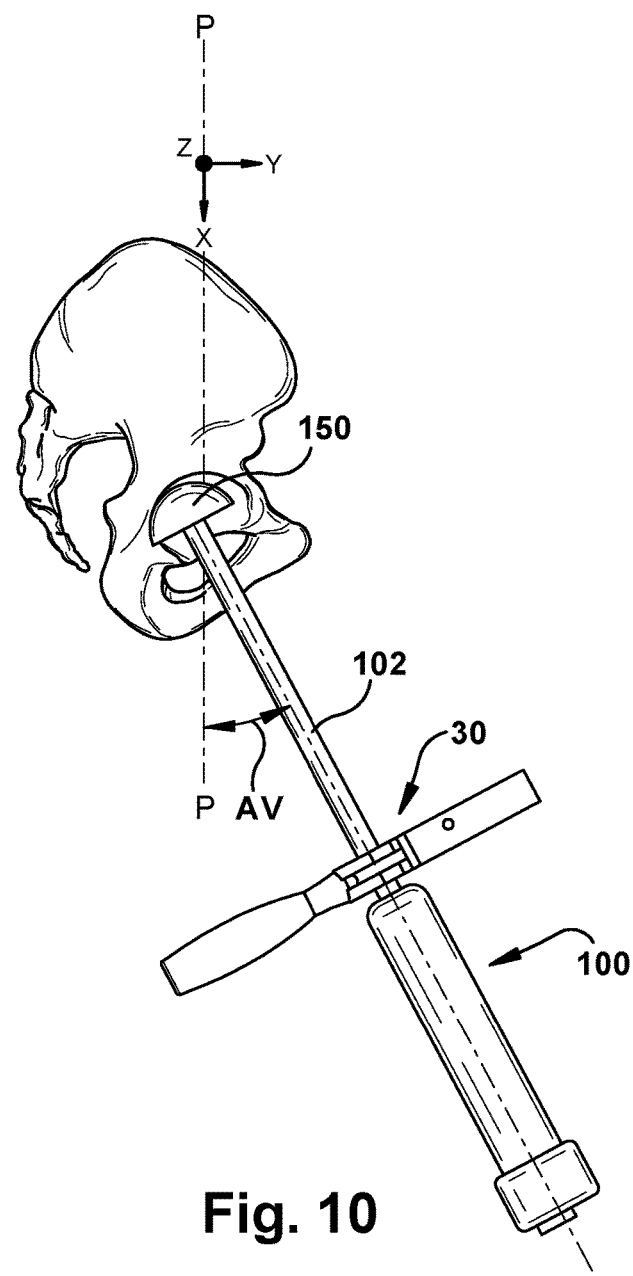
FIG. 10 is a lateral view of the pelvis in combination with the orientation sensor and the surgical instrument of FIG. 9.

FIGS. 9 and 10 illustrates the orientation sensor 30 in combination with the tool 100. As discussed above, the guide 124 may be configured to laterally receive the shaft 102 of the impactor relative to the central guide axis C and/or configured to longitudinally slide along the shaft 102. In an embodiment, the tool is an awl, a tap, or a screwdriver and the guide is configured receive the shaft of the awl, the tap, and/or the screwdriver and slide longitudinally along the corresponding shaft (e.g., until a handle of the awl abuts the orientation sensor). In some embodiments, the same orientation sensor is configured to mount to the shaft of the impactor, the awl, the tap, and/or the screwdriver.

The user input device 34 may be positioned on the display arm 126 such that a user gripping the handle 122 in the palm of one of the user's hands would be able to touch the user input device 34 with the thumb of the hand gripping the handle 122. For example, the user input device 34 may be disposed on a side of the display arm 126 at an end of the display arm 126 that is adjacent the guide 124.

As shown in FIGS. 9 and 10, the tool 100 may comprise a handle 122 and the shaft 102. An end of the shaft 102 opposite the handle 122 may be configured to hold an acetabular cup 150. For example, the end of the shaft 102 may be configured to expand to hold the acetabular cup 150, and configured to contract to release the acetabular cup 150.

In an embodiment, the orientation sensor is attachable to/detachable from or permanently integrated into the tool or another device, such as a surgical/medical device/equipment.

Turning to FIGS. 5-8, an example of setting a heading based on the orientation of the orientation sensor is represented. The processor 36 may be configured to, in response to the user input device 34 receiving the predetermined user input, set the heading based on the orientation of the orientation sensor 30 when the predetermined user input is received by the user input device 34.

Figure 5:
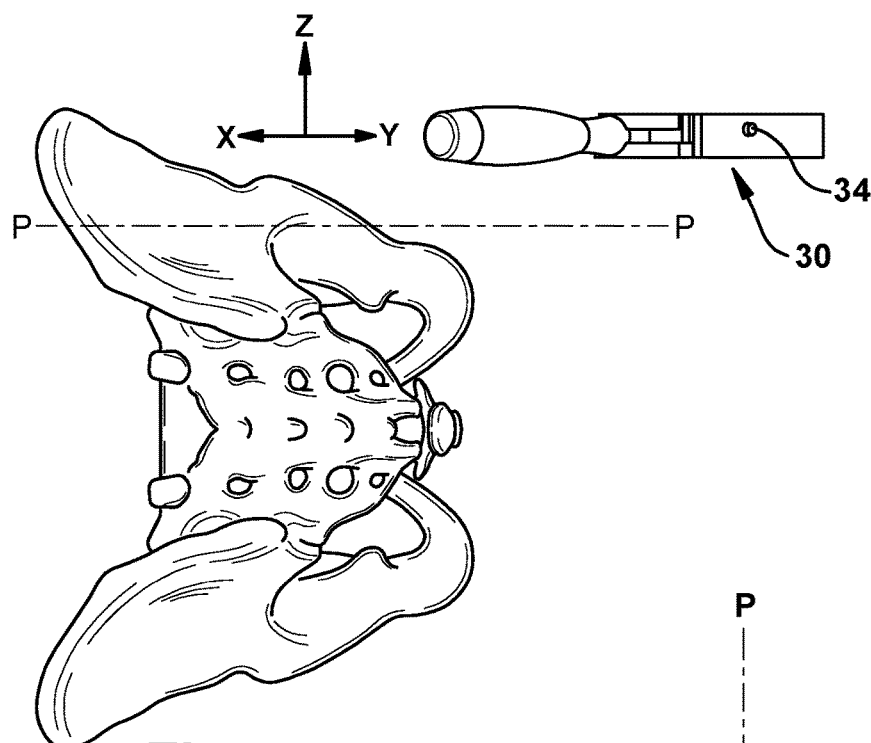
FIG. 5 is a posterior to anterior view of a pelvis in combination with the orientation sensor of FIG. 1 with an arbitrary heading.
Figure 6:
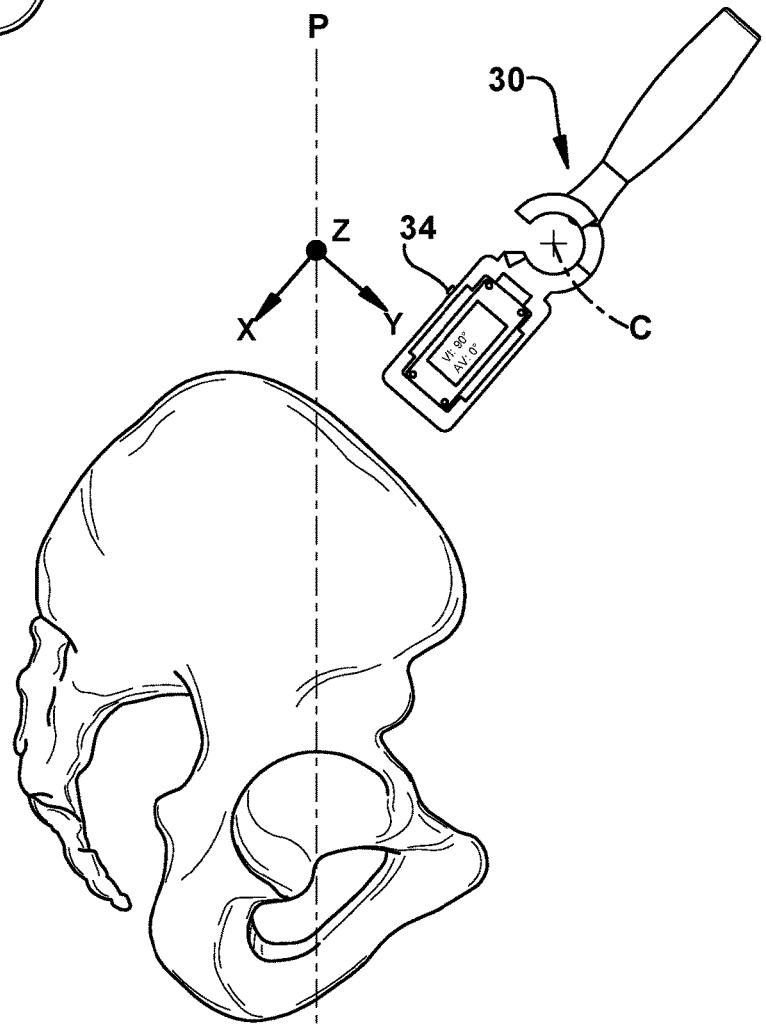
FIG. 6 is a lateral view of the pelvis in combination with the orientation sensor of FIG. 5.
Figure 7:
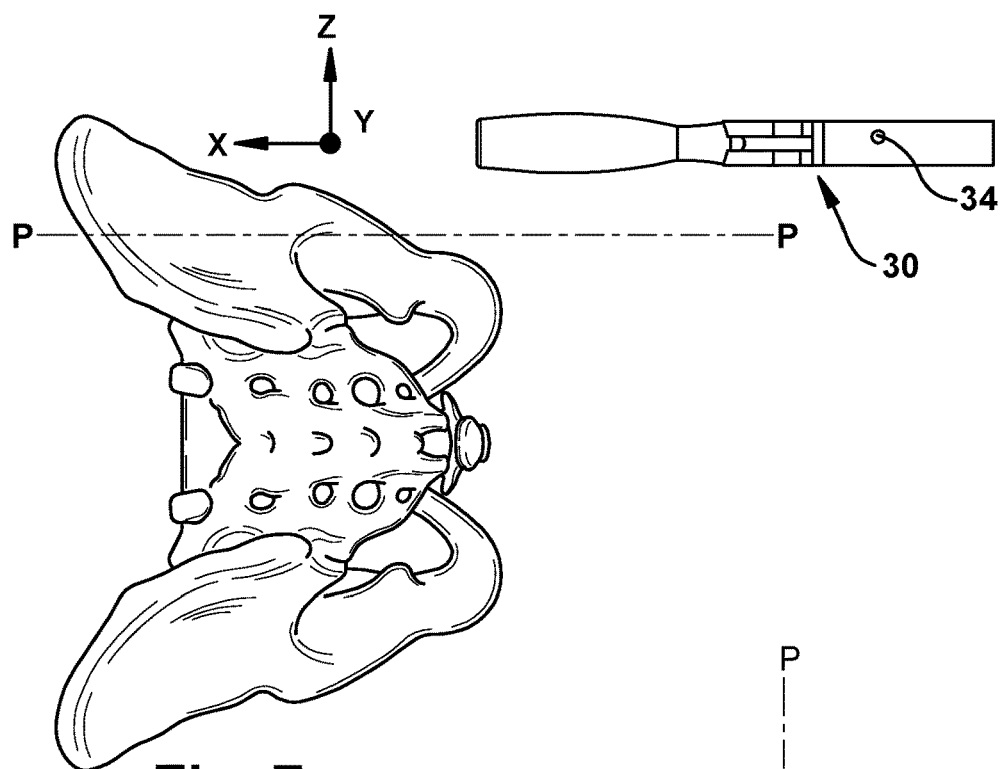
FIG. 7 is a posterior to anterior view of the pelvis in combination with the orientation sensor of FIG. 5 with a user-identified heading.
Figure 8:
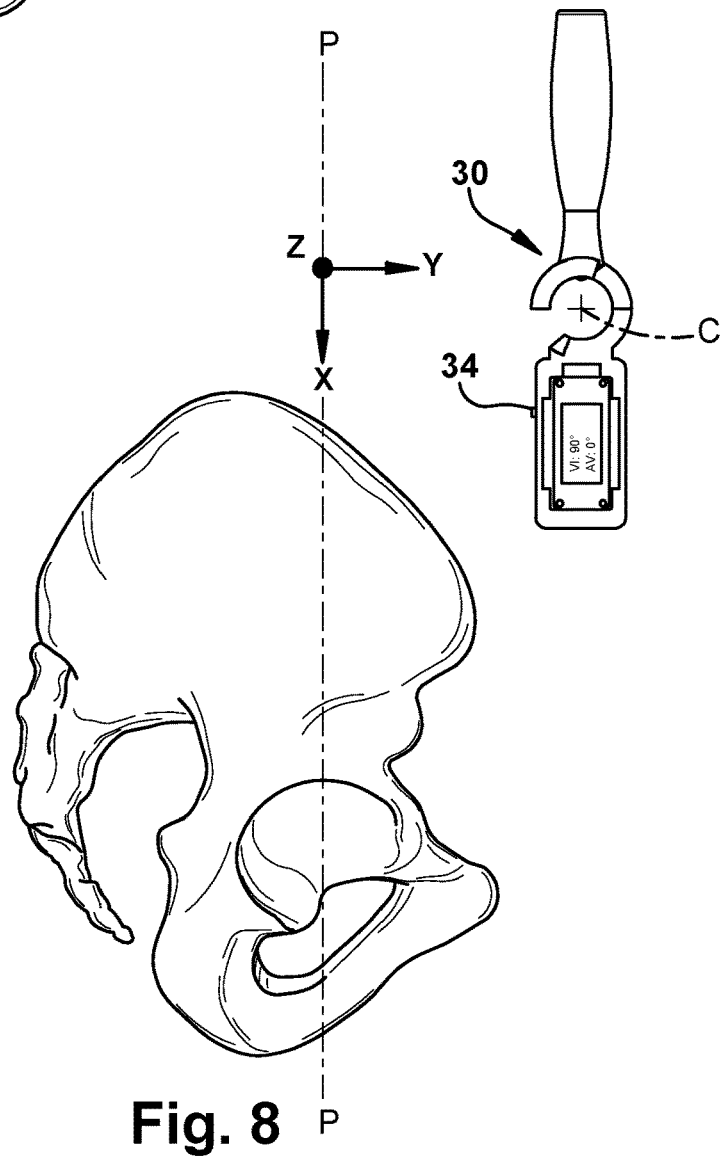
FIG. 8 is a lateral view of the pelvis in combination with the orientation sensor of FIG. 7.

The processor 36 may be to configured to associate the heading with a predetermined axis relative to the orientation sensor when the user presses the button. For example, when the heading is initially set to an undesired and arbitrary X-axis, as shown in FIGS. 5 and 6, that is not aligned with a desired axis (e.g., the longitudinal body axis P of the patient), the heading may be re-set to align or be associated with the longitudinal body axis P of the patient, as shown in FIGS. 7 and 8. The orientation of the X-axis (e.g., relative to the Earth) may not change based upon changing of the orientation of the orientation sensor 30 alone. Rather, the predefined user input (e.g., pressing the button) may cause the re-orientation of the coordinate system (e.g., associating the X-axis to the new heading).

The processor 36 may associate set the new heading by rotating the X-axis and the Y-axis about the Z-axis (e.g., the yaw axis) until the X-axis aligns with a plane defined by the Z-axis and the longitudinal sensor body axis L of the orientation sensor 30 (e.g., the processor is configured to zero rotation about the yaw axis). For example, as shown in FIGS. 7 and 8, the longitudinal sensor body axis L of the orientation sensor 30 may be aligned with the longitudinal body axis P of the patient (e.g., of the patient's pelvis), and while aligned the button 34 may be pressed, which causes the processor 36 to set the new heading by aligning the X-axis with the longitudinal sensor body axis L of the orientation sensor 30, thereby aligning the X-axis with the longitudinal body axis. The processor 36 may rotate the X-axis and the Y-axis about the Z-axis until the X-axis aligns with the longitudinal sensor body axis L to set the heading. After the heading is set, the heading may not change until the orientation sensor 30 is reset (e.g., by receiving additional user input, or by deactivating and reactivating the orientation sensor 30).

If the longitudinal axis is inclined relative to the X-Y plane (e.g., rotated about a pitch axis), the X-axis may be aligned with the longitudinal sensor body axis L such that the longitudinal axis maintains the inclination relative to the X-Y plane and is in the X-Z plane. Accordingly, if the X-Y plane represents a horizontal plane relative to the Earth prior to the heading being set, the X-Y plane continues to represent the horizontal plane after the heading is associated with the longitudinal sensor body axis L, even if the longitudinal axis is inclined relative to the horizontal plane.

When orientation sensor 30 is activated, the display 38 may indicate that a heading or axis needs to be chosen by the user. The processor 36 may be configured to receive the predetermined user input when the indication is present. For example, the display 38 may display the prompt "pick axis," and the processor 36 may be configured to receive the predetermined user input from the user pressing the button 34 when the prompt is displayed. In an embodiment, the heading may be set each time the predetermined user input is received.

The processor 36 may be configured to store the heading in the memory 50 in response to receiving the predetermined user input. The processor 36 may be configured to generate the orientation information based on the heading, that is stored in the memory 50, and the current orientation of the orientation sensor. As discussed below in relation to the orientations shown in FIGS. 11-14, the orientation sensor 30 does not need to be held flat in the orientation shown in FIG. 8—such that the central guide axis C is parallel with the Z-axis—to align the heading with the longitudinal body axis P.

Figure 15:
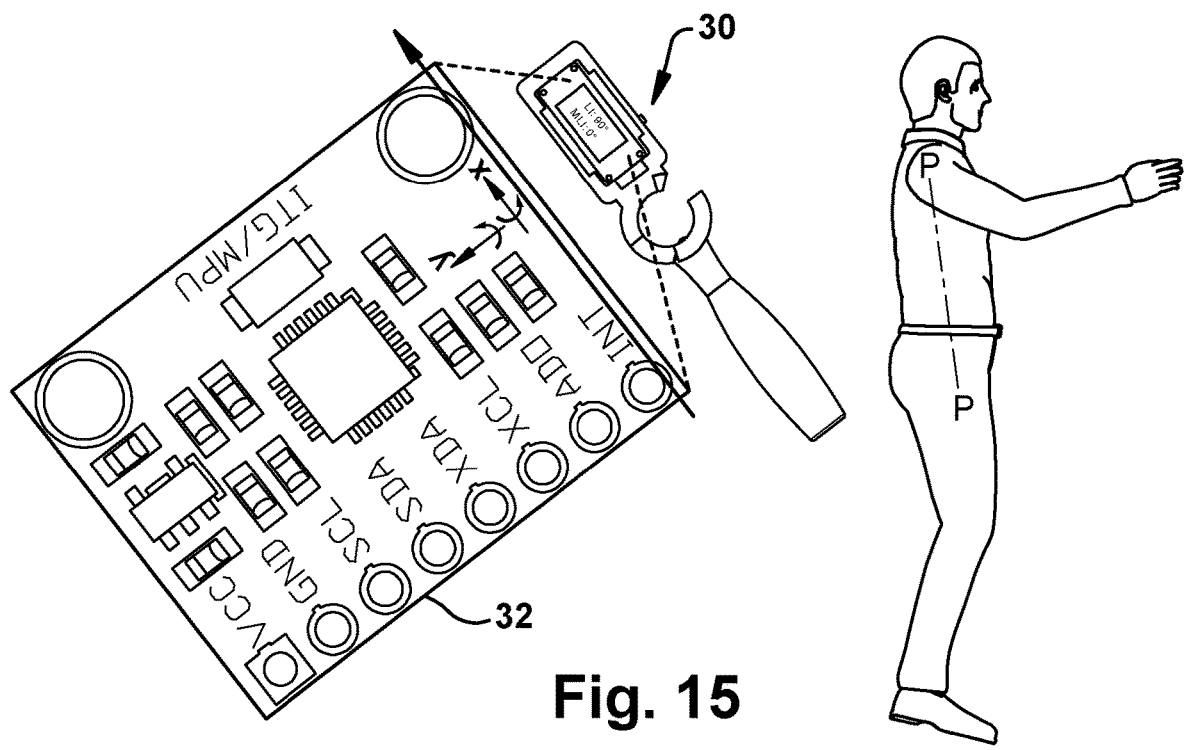
FIG. 15 is a top view of the orientation sensor of FIG. 1, with an arbitrary heading, in relation to an orientation sensing component of the orientation sensor and a longitudinal body axis of a patient lying on their side.

The heading may be associated with the orientation data such that when the orientation sensor 30 would be held in a predetermined reference orientation relative to the heading, the processor 36 generates predetermined orientation information and the display 38 displays a predetermined orientation value. For example, if the central guide axis C is entirely vertical (e.g., colinear or parallel with the Z-axis), processor may generate the predetermined orientation information such that the display 38 may display one or more predetermined angular values (e.g., a vertical inclination angle of 90° and an anteversion angle of 0° as shown in FIG. 8, or a longitudinal inclination angle of 90° and a medial-lateral inclination angle of 0° as shown in FIG. 15). If the orientation sensor is rotated from the predetermined reference orientation about the Y-axis (e.g., the pitch axis) by 45°, the display may display a vertical inclination angle of 45° (or a longitudinal inclination angle of 45°). If the orientation sensor 30 is further rotated about the Z-axis (e.g., the yaw axis) by 15° (e.g., such that the central guide axis C is inclined by 15° from the X-Z plane), the display may display an anteversion angle of 15° (or a medial-lateral inclination angle of 15°). Accordingly, changing the orientation of the orientation sensor, may result in a change in one or more of the orientation values displayed by the display 38. The displayed values may remain the same regardless of whether the orientation sensor 30 is rotated about the central guide axis C from a given position.

Turning to FIGS. 9 and 10, the orientation sensor 30 may be mounted to the shaft 102 (an example of an instrument body, or a portion of an instrument body) of the tool 100 such that the orientation sensor is at least partially fixed to the shaft 102. When the tool 100 is holding the acetabular cup 150 in a desired location of the pelvis, the heading has been set to the longitudinal body axis P of the patient, and the patient is lying on their side, the display 38 may display the vertical inclination and anteversion angles based on the orientation of the tool 100. For example, as the tool 100 is rotated about the Y-axis, as shown in FIG. 9, the display 38 may display the vertical inclination angle (or a longitudinal inclination angle) in real-time (e.g., 40° in the orientation shown in FIG. 9). As the tool 100 is inclined from the X-Z plane or rotated relative to the Z-axis, the display 38 may display the anteversion angle (or a medial-lateral inclination angle) in real-time (e.g., 15° in the orientation shown in FIG. 10). As discussed below, the heading may be set to an axis other than the longitudinal body axis P.

Turning to FIGS. 11-14, the orientation sensor 30 is illustrated in two different positions that may result in the same heading, as discussed above, when the button is pressed by the user (an example of the user input). For example, in FIG. 4 above, the longitudinal sensor body axis L and the display 38 are coplanar with a horizontal plane such that the display 38 faces in a direction along the Z-axis. When in this orientation, pressing the user input device 34 may set the heading by causing the processor 36 to align the X-axis with the horizontal component of the longitudinal sensor body axis L. The X-axis and the Y-axis may be rotated about the Z-axis until the X-axis aligns with the horizontal component of the longitudinal sensor body axis L (e.g., by saving the heading—e.g., at least the rotation about the Z-axis—in the memory 50).

Figure 11:
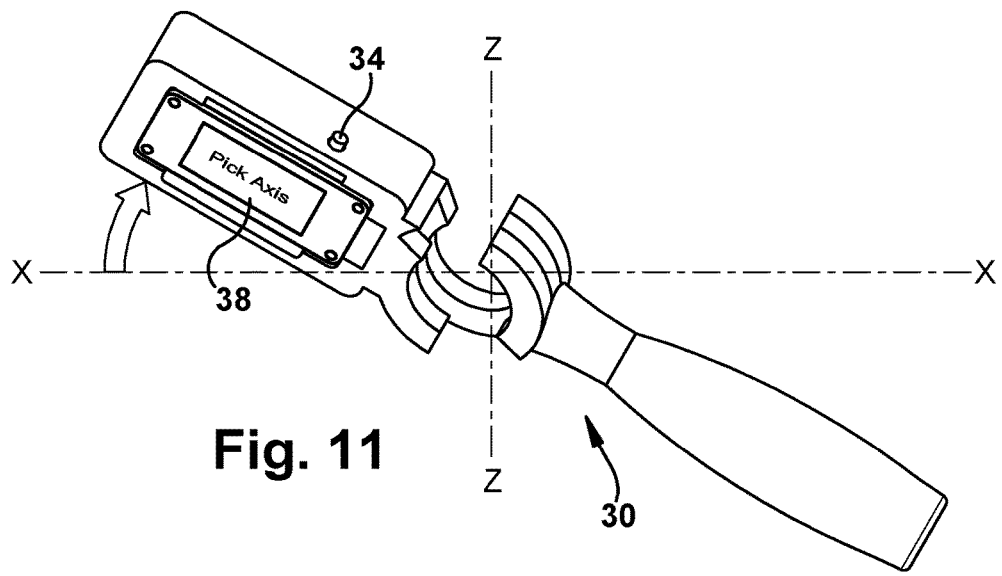
FIG. 11 is a side view of the orientation sensor of FIG. 1 in which the longitudinal sensor body axis of the orientation sensor is rotated about the X-axis, inclined relative to an X-axis and a Z-axis, and extends entirely in an X-Z plane.
Figure 12:
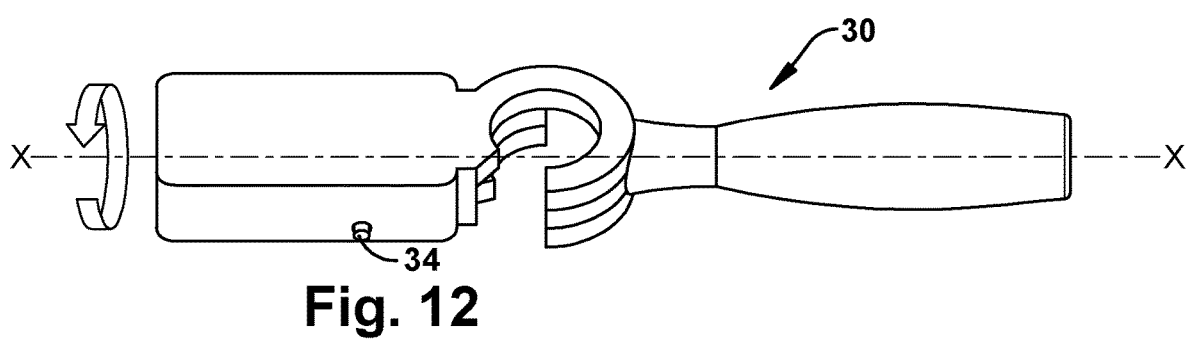
FIG. 12 is a top view of the orientation sensor in the orientation shown in FIG. 11.
Figure 13:
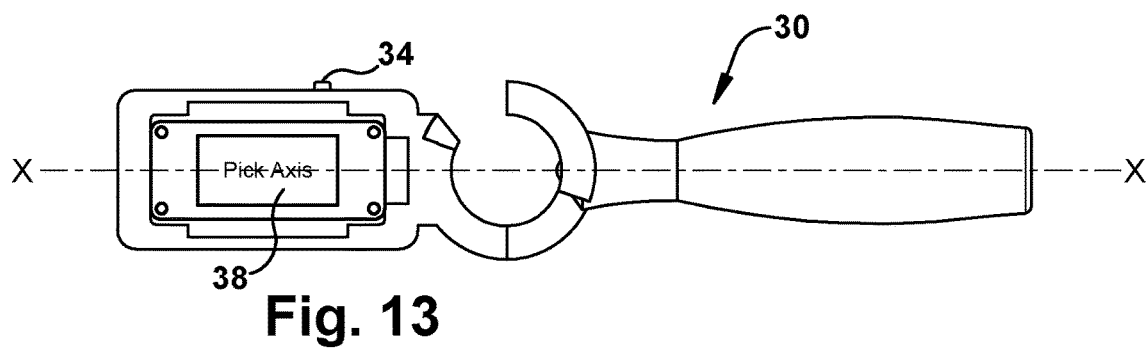
FIG. 13 is a side view of the orientation sensor of FIG. 11 in which the longitudinal sensor body axis of the orientation sensor is rotated about the X-axis from the orientation shown in FIG. 11, not inclined relative to an X-axis, and extends entirely in an X-Z plane.
Figure 14:
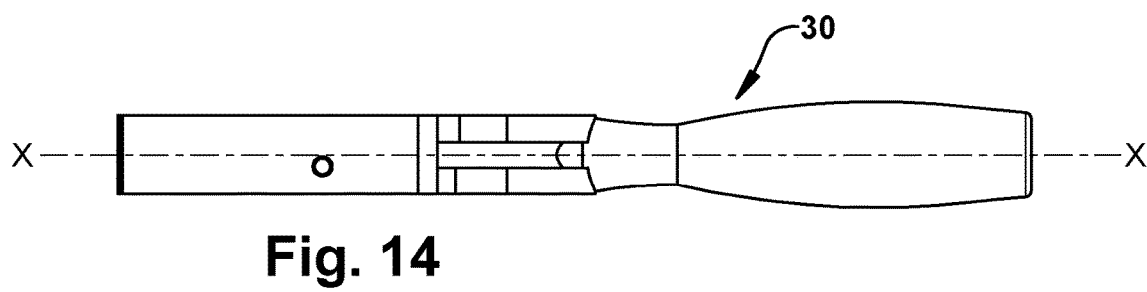
FIG. 14 a top view of the orientation sensor in the orientation shown in FIG. 13.

On the other hand, in FIGS. 11 and 12 the longitudinal sensor body axis L has been rotated relative to the X-axis, inclined relative to the X-axis and the Z-axis, and, similar to FIG. 4, extends entirely in the X-Z plane. In FIGS. 13 and 14, the longitudinal body axis L is rotated about the X-axis so that the display faces in a direction along the Y-axis, is not inclined relative to the X-axis, and extends entirely in the X-Z plane. Similar to the orientation shown in FIG. 4, when in the orientations shown in FIGS. 11-14, pressing the user input device 34 may set the heading by causing the processor 36 to align the X-axis with the horizontal component of the longitudinal sensor body axis L. The X-axis and the Y-axis may be rotated about the Z-axis until the X-axis aligns with the horizontal component of the longitudinal sensor body axis L (e.g., by saving the heading—e.g., at least or only the rotation about the Z-axis—in the memory 50).

Accordingly, in relation to a patient (e.g., lying in the position shown in FIG. 15) the orientation sensor 30 may be held in any of the positions shown in FIG. 4 or 11-14 such that the longitudinal sensor body axis L extends entirely in a plane defined by the desired axis of the patient (e.g., the longitudinal body axis P) and the vertical axis (e.g., the Z-axis). Pressing the user input device 34 when the longitudinal sensor body axis L extends entirely in the plane defined by the desired axis and the vertical axis (e.g., in any of the positions shown in FIG. 4 or 11-14), may cause the processor 36 to align the X-axis with such plane. For example, by keeping the X-axis at its current alignment shown in FIGS. 11-14, if the heading is already set to the direction shown in FIGS. 11-14 (e.g., the orientation of the X-axis). If, instead, the heading was previously set to a different direction than shown in FIGS. 11-14 (e.g., if the X-axis is aligned in a different direction relative to the orientation sensor 30), pressing the user input device 34 while the orientation sensor is in any of the orientations shown in FIGS. 11-14 may cause the processor 36 to rotate the X-axis and the Y-axis about the Z-axis until the X-axis aligns with the plane defined by the by the desired axis and the vertical axis (e.g., by saving the heading—e.g., at least or only the rotation about the Z-axis—in the memory 50).

Figure 16:
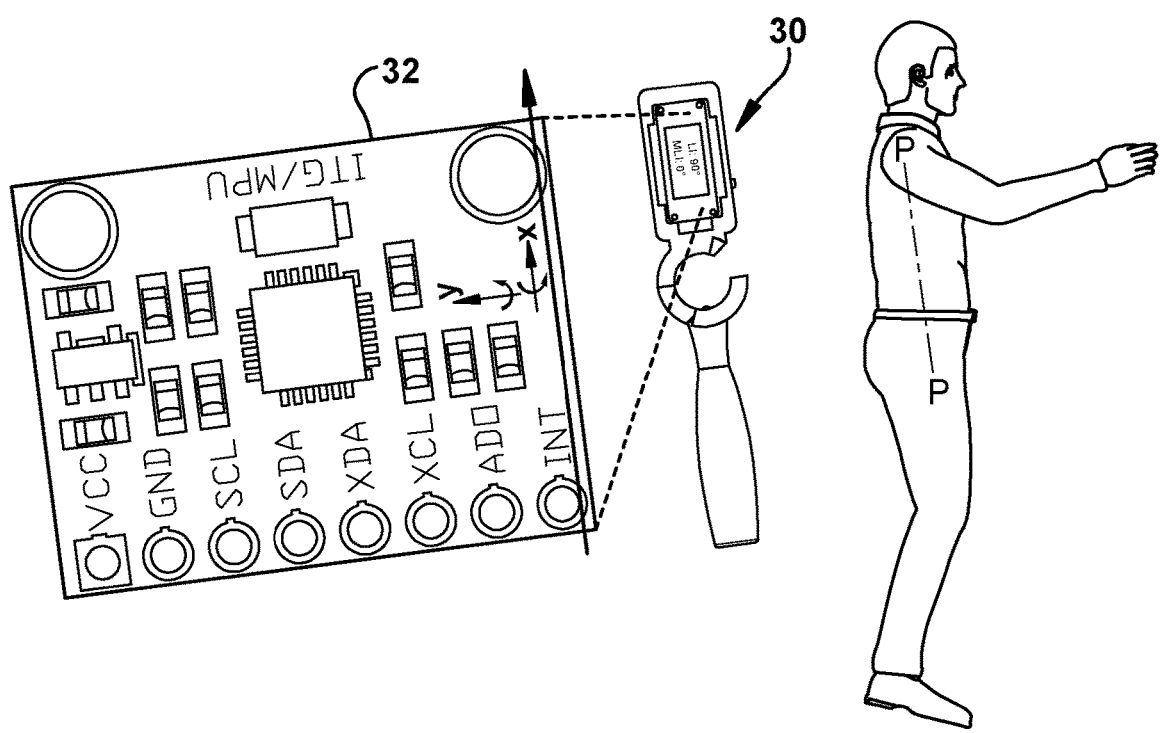
FIG. 16 is a top view of the orientation sensor, with user-identified heading, in relation to the orientation sensing component and the longitudinal body axis FIG. 15.

FIGS. 15-21 provide other representative examples of headings that the orientation sensor may be set to in relation to the orientation of the IMU 32 of the orientation sensor 30. The orientation of the IMU 32 relative to the orientation of the orientation sensor 30 is exemplified in FIGS. 15-21 (as discussed above, the IMU 32 may be disposed within the body of the orientation sensor 30, as represented by dashed lines in FIGS. 15-21). FIGS. 15 and 16 illustrate a patient that is lying on their side with the longitudinal body axis P extending from their shoulder to their hip. As discussed above, the orientation sensor may have a heading set in a direction that is undesirably misaligned with the longitudinal body axis P, as exemplified with the arrow along the IMU in FIG. 15. The heading of the orientation sensor may be set to the longitudinal body axis by aligning the longitudinal sensor body axis L of the orientation sensor 30 with the longitudinal body axis, as shown in FIG. 16, and then providing the predetermined user input to the user input device 34.

Figure 17:
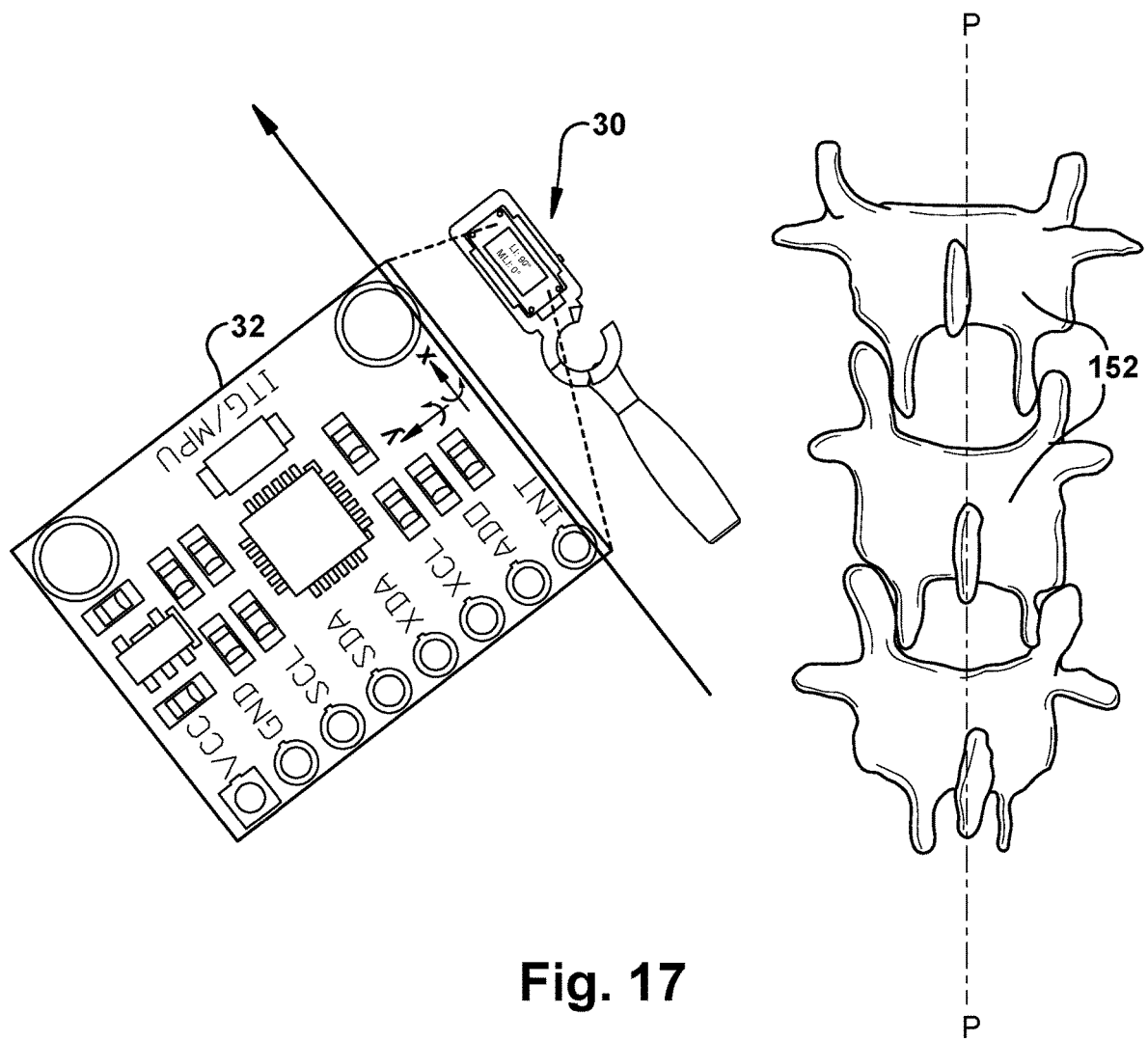
FIG. 17 is a top view of the orientation sensor of FIG. 1, with an arbitrary heading, in relation to an orientation sensing component of the orientation sensor and a longitudinal body axis of a patient's spinous process.
Figure 18:
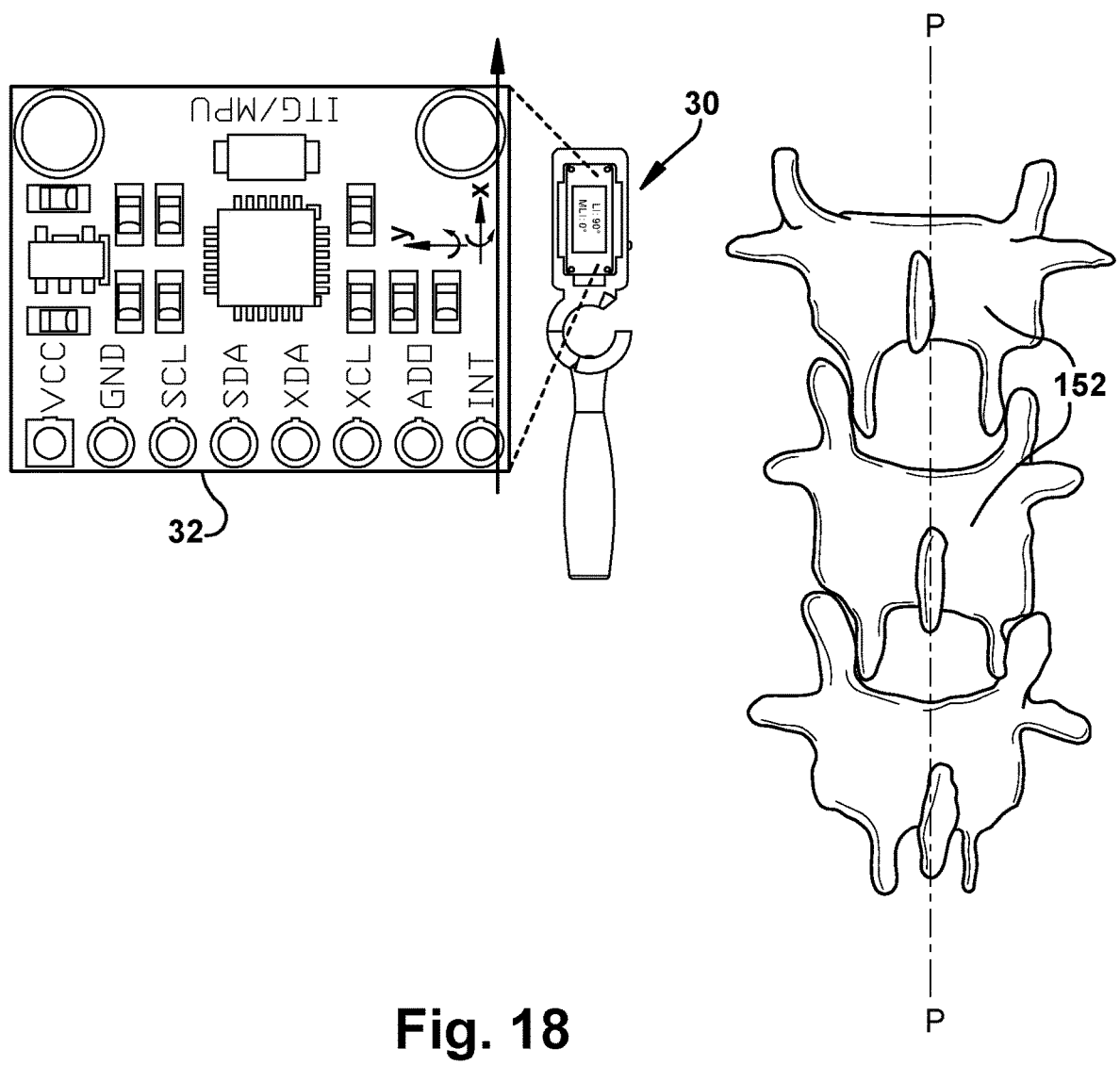
FIG. 18 is a top view of the orientation sensor, with user-identified heading, in relation to the orientation sensing component and the longitudinal body axis FIG. 17.

FIGS. 17 and 18 illustrate multiple vertebrae 152 of a patient. The desired longitudinal body axis may extend along one or more of the spinous processes of the vertebrae.

Similar to the above, the orientation sensor may have a heading set in a direction that is undesirably misaligned with the longitudinal body axis P, as exemplified with the arrow along the IMU in FIG. 17. The heading of the orientation sensor may be set to the longitudinal body axis by aligning the longitudinal sensor body axis L of the orientation sensor 30 with the longitudinal body axis, as shown in FIG. 18, and then providing the predetermined user input to the user input device 34. In an embodiment, the longitudinal body axis extends along a center of the vertebral bodies of the patient.

Figure 19:
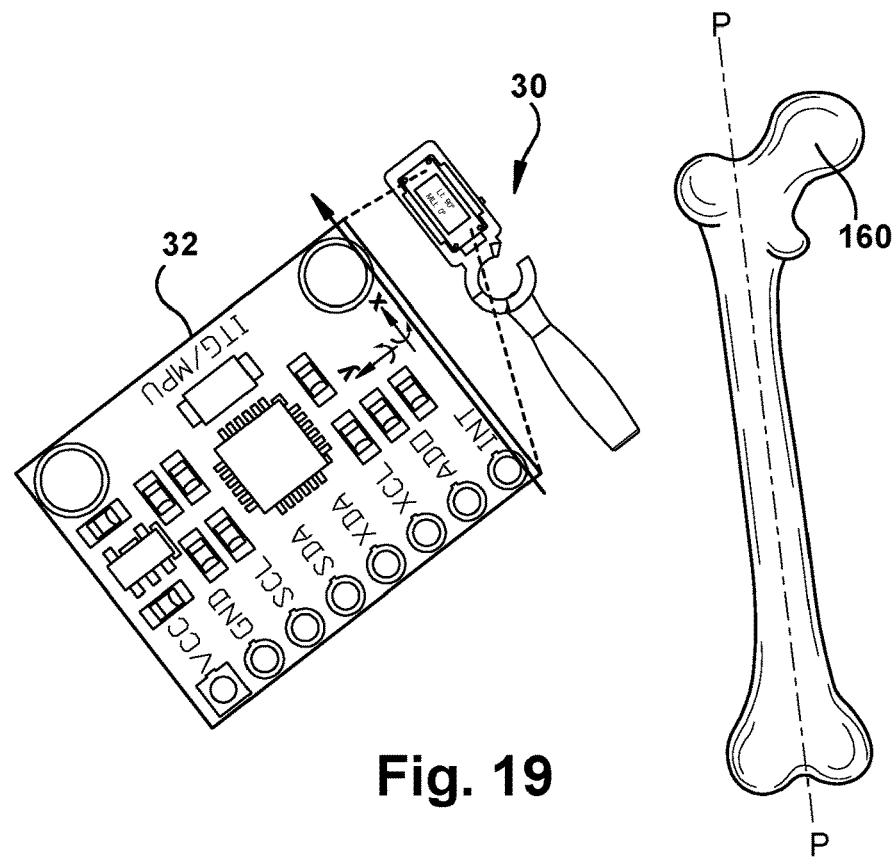
FIG. 19 is a top view of the orientation sensor of FIG. 1, with an arbitrary heading, in relation to an orientation sensing component of the orientation sensor and a longitudinal body axis of a patient's bone.
Figure 20:
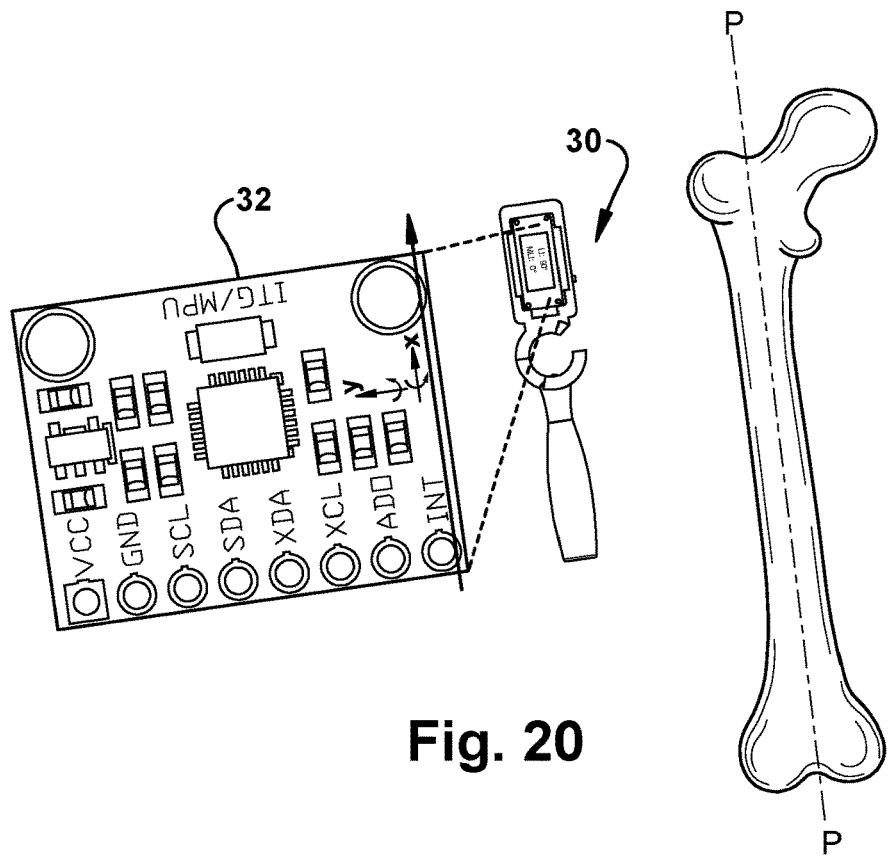
FIG. 20 is a top view of the orientation sensor, with user-identified heading, in relation to the orientation sensing component and the longitudinal body axis FIG. 19.
Figure 21:
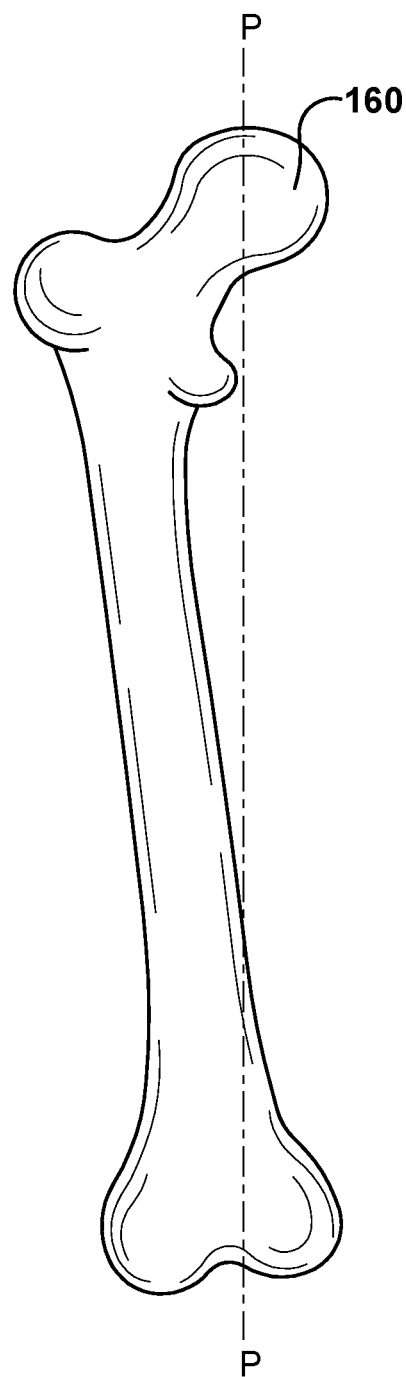
FIG. 21 is top view of the patient's bone of FIG. 19 with an alternative longitudinal body axis.

FIGS. 19-21 illustrate a bone 160 of a patient. The desired longitudinal body axis may extend along the anatomical axis of the bone 160, as shown in FIGS. 19 and 20, or may extend along the mechanical axis of the bone 160, as shown in FIG. 21. Similar to the above, the orientation sensor 30 may have a heading set in a direction that is undesirably misaligned with the longitudinal body axis P, as exemplified with the arrow along the IMU in FIG. 19. The heading of the orientation sensor may be set to the longitudinal body axis by aligning the longitudinal sensor body axis L of the orientation sensor 30 with the desired longitudinal body axis P, as shown in FIG. 20, or in a similar manner for the longitudinal body axis of FIG. 21, and then providing the predetermined user input to the user input device 34.

The processor 36 may be configured to determine whether the orientation of the orientation sensor is within a predetermined threshold of a predetermined alignment orientation. For example, the predetermined alignment orientation may include a vertical inclination of 40° relative to the X-Y plane and includes an anteversion angle of 15° relative to the X-Z plane. The threshold for each value may be +/−10°. Accordingly, if the vertical inclination of the orientation sensor 30 is anywhere from 30° to 50° and/or the anteversion angle of the orientation sensor 30 is anywhere from 5° to 25°, the processor 36 may determined that the orientation is within the predetermined threshold of the predetermined alignment orientation.

In an embodiment, the one or more lights of the light source turn on/off or pulse based on whether the orientation of the tool is within a predetermined threshold of the predetermined alignment orientation. For example, a lower light can be turned off when the handle of the tool is too low, thereby informing the user that the handle needs to be raised to reach the predetermined alignment orientation.

In an embodiment, one or more lights of the light source change color based on whether the orientation of the tool is within a predetermined threshold of the predetermined alignment orientation. A red, yellow, or green color may indicate that the tool is out of position, close to position, or within a position (or within a predetermined threshold of the position) that is designated (e.g., by the user). For example, a green light may be generated when the orientation is within the predetermined threshold, and a red light may be generated when the orientation is outside of the predetermined threshold. The red light may be directed downward and/or a green light may be directed upward when the handle of the tool is too low to provide the user with feedback regarding how the orientation of the tool should be to better match the predetermined alignment orientation.

In some embodiments, the light source is configured to adjust based on a predetermined fixed angle or position value. For example, one or more lights of the lights source may light up in a predetermined orientation, sequence, and/or pattern to indicate that the tool is being used at the predetermined alignment orientation or a predetermined orientation relative to a designated orientation.

For example, the processor may be configured to receive a user input of a desired orientation in the x, y, z planes, and the instrument lighting can turn on/off and change color intermittently based on the current orientation to provide feedback to the user about the orientation. Independent differential feedback in each plane that can account for degrees of misalignment from the predetermined orientation can indicate to the user how to adjust the instrument to reach the predetermined orientation.

In some embodiments, the orientation sensor and/or the surgical awl is configured to provide audio and/or tactile feedback to the user based on whether the orientation of the tool is within the predetermined threshold of the predetermined alignment orientation.

As mentioned above, features of any of the above aspects may be combined with one another. For example, the tool may include a detachable orientation sensor that is partially fixable relative to an instrument body, or the tool may include an integrated orientation sensor. The tool may provide feedback (e.g., a digital read-out and/or light feedback) based on the orientation sensed by the orientation sensor and the heading set by the user.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An orientation sensor comprising:
   a processor;
   an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component;
   a display operably coupled to the processor, wherein the display is configured to display at least one orientation value, that is associated with the plurality of orientation data, in real-time;
   a user input device operably coupled to the processor, wherein the processor is configured to, in response to the user input device receiving a predetermined user input, set a heading based on the orientation of the orientation sensor when the predetermined user input is received by the user input device;

wherein the heading is associated with the orientation data such that when the orientation sensor would be held in a predetermined reference orientation relative to the heading, the display displays a predetermined orientation value, and whereby movement of the orientation sensing component in the at least one direction from the predetermined reference orientation would be represented on the display as the at least one orientation value being different from the predetermined orientation value.

2. The orientation sensor of claim 1, wherein the orientation data includes rotation data relative to an X-axis, a Y-axis, and a Z-axis, the Y-axis being perpendicular to the X-axis, and the Z-axis being perpendicular to the X-axis and the Y-axis; and wherein the heading is associated with the X-axis.

3. The orientation sensor of claim 2, wherein the X-axis and the Y-axis define a horizontal plane relative to the Earth, and the Z-axis is vertical relative to the Earth.

4. The orientation sensor of claim 3, wherein the orientation data includes rotation data representation rotation of the orientation sensor about the Y-axis and the Z-axis.

5. The orientation sensor of claim 2, wherein the processor is configured to, in response to the user input device receiving the predetermined user input, set the heading to be horizontal relative to the Earth and entirely within a plane that is parallel to i) the X-axis; and ii) a plane that is parallel to the longitudinal axis of the orientation sensor and the Z-axis.

6. The orientation sensor of claim 2, wherein the processor is configured to, in response to the user input device receiving the predetermined user input, set the heading by only zeroing a rotation about the Z-axis.

7. The orientation sensor of claim 2, wherein the processor is configured to output to the display orientation information that includes an angle of inclination relative to an X-Z plane and/or relative to an X-Y plane, and wherein the at least one orientation value includes the angle of inclination relative to the X-Z plane and/or relative to the X-Y plane.

8. The orientation sensor of claim 2, wherein the orientation sensor includes a guide configured to mount to a shaft of the instrument body, wherein the guide defines a guide axis;

wherein the processor is configured to, in response to the user input device receiving the predetermined user input, set the heading to be horizontal relative to the Earth and entirely within a plane that is parallel to i) the X-axis; and ii) a plane that is parallel to the longitudinal axis of the orientation sensor and the Z-axis;

wherein the processor is configured to, in response to the user input device receiving the predetermined user input, set the heading by only zeroing a rotation about the Z-axis;

wherein the processor is configured to output to the display orientation information that includes an angle of inclination of the guide axis relative to an X-Z plane and/or relative to an X-Y plane based on the heading, and wherein the at least one orientation value includes the angle of inclination of the guide axis relative to the X-Z plane and/or relative to the X-Y plane based on the heading.

9. The orientation sensor of claim 1, wherein the display is configured to display orientation information, that is based on at least part of the orientation data, as one or more angular values based on the heading.

10. The orientation sensor of claim 1, wherein the plurality of orientation data includes pitch data, roll data, and yaw data, and wherein when the orientation sensor is in the predetermined reference orientation relative to the heading, the orientation information represents a zeroed yaw orientation.

11. The orientation sensor of claim 1, wherein the user input device is a touch input device.

12. A surgical instrument including:
an instrument body;
the orientation sensor of claim 1, wherein the orientation sensor is configured to mount to the instrument body, and wherein orientation sensing component is configured to be removable from the instrument body by hand;
wherein the orientation information includes rotation data representing rotation of the orientation sensor about the Y-axis and the Z-axis, and the display is configured to display a representation of the rotation about the Y-axis and the Z-axis; and
wherein the processor is configured such that when the orientation sensor is mounted to the instrument body, rotation of the entire orientation sensor about a shaft axis of the instrument body does not alter the representation of the orientation information that is displayed on the display.

13. A method of aligning the instrument of claim 12, including:
inputting the predetermined user input to the user input device while an axis of the orientation sensor is aligned with an axis of the patient;
moving the surgical tool to a predetermined position in the patient and orienting the orientation sensor to the predetermined alignment orientation.

14. An orientation sensor comprising:
a processor;
a memory operably coupled to the processor;
an orientation sensing component operably coupled to the processor, wherein the orientation sensing component is configured to detect a plurality of orientation data, wherein the orientation sensor is configured to be mounted to an instrument body such that when the orientation sensor is mounted to the instrument body the orientation sensing component would be at least partially fixed relative to the instrument body such that a change in orientation of the instrument body in at least one direction would be detected by the orientation sensing component;
a user input device operably coupled to the processor, wherein, in response to the user input device receiving a predetermined user input, the processor is configured to store, in the memory, a heading based on the orientation of the orientation sensor when the predetermined user input is received by the user input device;
wherein the processor is configured to generate orientation information based on the heading, that is stored in the memory, and the current orientation of the orientation sensor; and
wherein the heading is associated with the orientation data such that when the orientation sensor would be held in a predetermined reference orientation relative to the heading, processor generates predetermined orientation information, and whereby movement of the orientation sensing component in the at least one direction from the predetermined reference orientation would be represented by the processor generating a first orientation information that is different from the predetermined orientation information.

15. The orientation sensor of claim 14, wherein the orientation information includes rotation data relative to an X-axis, a Y-axis, and a Z-axis, the Y-axis being perpendicular to the X-axis, and the Z-axis being perpendicular to the X-axis and the Y-axis;
wherein the heading is associated with the X-axis.

16. The orientation sensor of claim 15, wherein the processor is configured to only set the X-axis when setting the heading, whereby the Y-axis remains perpendicular to the X-axis, and the Z-axis remains unchanged and perpendicular to both the X-axis and the Y-axis, wherein the X-axis and the Y-axis define a horizontal plane relative to the Earth, and the Z-axis is vertical relative to the Earth.

17. The orientation sensor of claim 15, wherein the orientation information includes rotation data representation rotation of the orientation sensor about the Y-axis and the Z-axis.

18. The orientation sensor of claim 15, wherein the orientation sensor includes a guide configured to mount to a shaft of the instrument body, wherein the guide defines a guide axis;
wherein the processor is configured to, in response to the user input device receiving the predetermined user input, set the heading to be horizontal relative to the Earth and entirely within a plane that is parallel to i) the X-axis; and ii) a plane that is parallel to the longitudinal axis of the orientation sensor and the Z-axis;
wherein the processor is configured to, in response to the user input device receiving the predetermined user input, set the heading by only zeroing a rotation about the Z-axis;
wherein the processor is configured to output orientation information that includes an angle of inclination of the guide axis relative to an X-Z plane and/or relative to an X-Y plane based on the heading.

19. The orientation sensor of claim 14, wherein the processor is configured to generate the orientation information as one or more angular values based on the heading.

20. The orientation sensor of claim 19, further including a display that is operably coupled to the processor, wherein the display is configured to display the one or more angular values based on the heading.

21. The orientation sensor of claim 14, wherein the plurality of orientation data includes pitch data, roll data, and yaw data, and wherein when the orientation sensor is in the predetermined reference orientation relative to the heading, the orientation information represents a zeroed yaw orientation.

22. The orientation sensor of claim 14, wherein the processor is configured to determine whether the orientation of the orientation sensor is within a predetermined threshold of a predetermined alignment orientation, and the processor is configured to provide audio, tactile, and or visual feedback in response to the determination of whether the orientation of the orientation sensor is within the predetermined threshold.

23. The orientation sensor of claim 14, wherein the user input device is a touch input device.

24. The orientation sensor of claim 14, wherein the processor is configured to set the heading at the time of receipt of the predetermined user input.

25. A surgical instrument including:
an instrument body;
the orientation sensor of claim 14, wherein the orientation sensor is configured to mount to the instrument body, and wherein orientation sensing component is configured to be removable from the instrument body by hand;
wherein the orientation information includes rotation data representation rotation of the orientation sensor about the Y-axis and the Z-axis; and
wherein the processor is configured such that when the orientation sensor is mounted to the instrument body, rotation of the entire orientation sensor about a shaft axis of the instrument body does not alter the orientation information.

26. A method of aligning the instrument of claim 25, including:
inputting the predetermined user input to the user input device while an axis of the sensor is aligned with an axis of the patient,
moving the surgical tool to a predetermined position in the patient and orienting the orientation sensor to the predetermined alignment orientation.

* * * * *